(12) United States Patent
Shipp

(10) Patent No.: US 10,869,656 B2
(45) Date of Patent: *Dec. 22, 2020

(54) VESSEL SEALING DEVICE WITH AUTOMATIC DEPLOYMENT

(71) Applicant: Cyndrx, LLC, Brentwood, TN (US)

(72) Inventor: John I. Shipp, Jacksonville, FL (US)

(73) Assignee: Cyndrx, LLC, Brentwood, TN (US)

( * ) Notice: Subject to any disclaimer, the term of this patent is extended or adjusted under 35 U.S.C. 154(b) by 119 days.

This patent is subject to a terminal disclaimer.

(21) Appl. No.: 16/253,110

(22) Filed: Jan. 21, 2019

(65) Prior Publication Data

US 2019/0175160 A1   Jun. 13, 2019

Related U.S. Application Data

(63) Continuation of application No. 14/852,539, filed on Sep. 12, 2015, now Pat. No. 10,182,803, which is a continuation of application No. 13/746,276, filed on Jan. 21, 2013, now Pat. No. 9,131,931.

(51) Int. Cl.
*A61B 17/00* (2006.01)
*A61B 90/00* (2016.01)

(52) U.S. Cl.
CPC .......... *A61B 17/0057* (2013.01); *A61B 90/03* (2016.02); *A61B 2017/00623* (2013.01); *A61B 2017/00659* (2013.01); *A61B 2090/037* (2016.02)

(58) Field of Classification Search
CPC ..... A61B 17/0057; A61B 17/10; A61B 17/11; A61B 17/115; A61B 17/1152; A61B 17/1155; A61B 17/0401; A61B 2017/00575; A61B 2017/00579; A61B 2017/00588; A61B 2017/00592; A61B 2017/00606; A61B 2017/0061; A61B 2017/00619; A61B 2017/00623; A61B 2017/00637; A61B 2017/00641; A61B 2017/0065; A61B 2017/00654; A61B 2017/00659; A61B 2017/00663; A61B 2017/00668; A61B 2017/00672; A61B 2017/1157; A61B 2017/1107

See application file for complete search history.

(56) References Cited

U.S. PATENT DOCUMENTS

| | | |
|---|---|---|
| 5,342,393 A | 8/1994 | Stack |
| 5,350,399 A | 9/1994 | Erlebacher et al. |
| 5,620,461 A | 4/1997 | Muijs Van De Moer et al. |
| 6,022,351 A | 2/2000 | Bremer et al. |
| 6,045,569 A | 4/2000 | Kensey et al. |
| 6,090,130 A | 7/2000 | Nash et al. |
| 7,175,646 B2 | 1/2007 | Brenneman et al. |
| 7,250,057 B2 | 7/2007 | Forsberg |
| 7,335,220 B2 | 2/2008 | Khosravi et al. |
| 7,488,340 B2 | 2/2009 | Kauphusman et al. |
| 7,597,705 B2 | 10/2009 | Forsberg et al. |

(Continued)

*Primary Examiner* — Katherine H Schwiker
(74) *Attorney, Agent, or Firm* — Michael L. Leetzow, P.A.

(57) ABSTRACT

A device and a method for sealing an opening in the wall of a blood vessel is provided. The device includes an automatic mechanism, a shaft fixedly connected to the automatic mechanism, a seal assembly attached to the distal end of the shaft, and a pushing rod also engaging the seal assembly, the automatic mechanism moving the pushing rod from a first position to a second position in response to the shaft being pulled distally a predetermined distance.

12 Claims, 16 Drawing Sheets

(56) References Cited

U.S. PATENT DOCUMENTS

| | | |
|---|---|---|
| 7,618,438 B2 | 11/2009 | White et al. |
| 7,850,710 B2 | 12/2010 | Huss |
| 7,931,670 B2 | 4/2011 | Fiehler et al. |
| 7,988,706 B2 | 8/2011 | Forsberg |
| 8,029,533 B2 | 10/2011 | Bagaoisan et al. |
| 8,048,108 B2 | 11/2011 | Sibbitt, Jr. et al. |
| 8,075,589 B2 | 12/2011 | Pipenhagen et al. |
| 8,080,034 B2 | 12/2011 | Bates et al. |
| 8,128,632 B2 | 3/2012 | Paris et al. |
| 8,128,652 B2 | 3/2012 | Paprocki |
| 8,128,653 B2 | 3/2012 | McGuckin, Jr. et al. |
| 9,131,931 B2 * | 9/2015 | Shipp ................ A61B 17/0057 |
| 10,182,803 B2 * | 1/2019 | Shipp ................ A61B 17/0057 |
| 2001/0007077 A1 | 7/2001 | Ginn et al. |
| 2002/0002386 A1 | 1/2002 | Ginn et al. |
| 2003/0078598 A1 | 4/2003 | Ginn et al. |
| 2006/0195123 A1 | 8/2006 | Ginn et al. |
| 2006/0195124 A1 | 8/2006 | Ginn et al. |
| 2006/0265007 A1 | 11/2006 | White et al. |
| 2006/0271078 A1 | 11/2006 | Modesitt |
| 2007/0060895 A1 | 3/2007 | Sibbitt, Jr. et al. |
| 2007/0185529 A1 | 8/2007 | Coleman et al. |
| 2008/0109030 A1 | 5/2008 | Houser et al. |
| 2008/0243182 A1 | 10/2008 | Bates et al. |
| 2009/0254119 A1 | 10/2009 | Sibbett, Jr. et al. |
| 2010/0087854 A1 | 4/2010 | Stopek et al. |
| 2010/0305601 A1 | 12/2010 | Karbowniczek et al. |
| 2011/0066181 A1 | 3/2011 | Jenson et al. |
| 2012/0022585 A1 | 1/2012 | Atanasoska et al. |

* cited by examiner

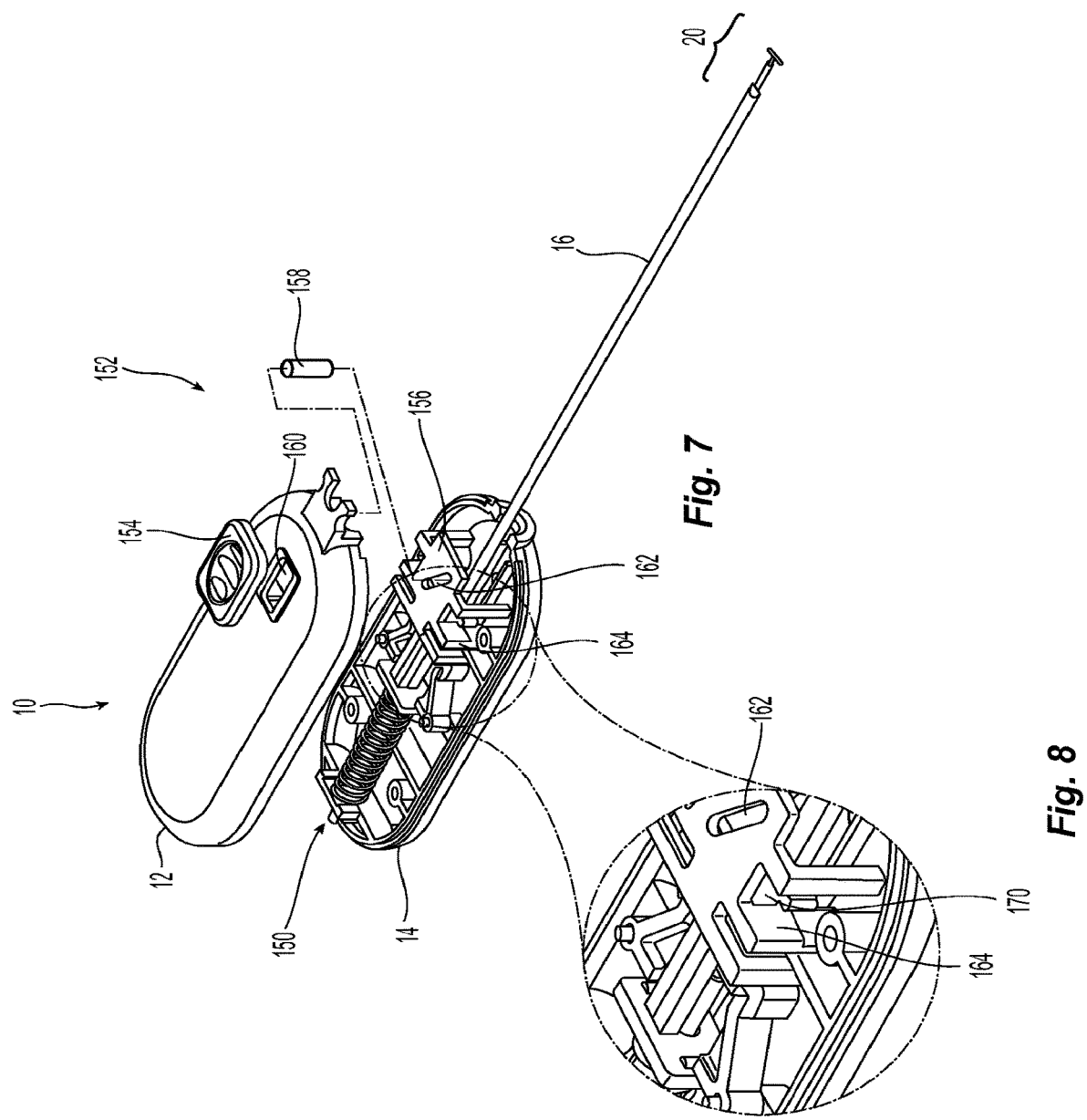

VESSEL SEALING DEVICE WITH AUTOMATIC DEPLOYMENT

This application is a continuation application of and claims priority to U.S. patent application Ser. No. 13/746,276, filed Jan. 21, 2013, and to U.S. patent application Ser. No. 14/852,539, filed on Sep. 12, 2015, the contents of which are hereby incorporated by reference in their entirety.

BACKGROUND OF THE INVENTION

Field of the Invention

The present invention relates generally to a sealing device for the closure of puncture holes in blood vessels and, in particular, to a sealing device that does not require a sheath change and is simple with an automatic feature.

Technical Background

For many diagnostic and interventional procedures it is necessary to access arteries or veins. Vessel access is accomplished either by direct vision or percutaneously. In either case, the target vessel is punctured with a hollow needle containing a tracer wire. When the intravascular positioning of the tracer wire has been verified, the hollow needle is removed leaving the tracer wire. Next, a sheath containing a dilator is pushed in over the tracer wire. The dilator enlarges the puncture opening to facilitate the insertion of the larger diameter sheath into the blood vessel. The sheath usually consists of a hollow tube with an open distal end and a hemostatic valve at a proximal end, which remains outside the body and blood vessel. The hemostatic valve is made of a compliant material and is designed in such a way as to allow devices such as catheters to be inserted and withdrawn from the blood vessel with minimal blood loss. After the sheath has been inserted into the blood vessel, the dilator is removed leaving a clear passageway in the sheath for the catheter. The sheath is removed from the blood vessel after the procedure is finished resulting in bleeding at the puncture site that must be staunched.

Traditionally, pressure is applied to the puncture site to allow time for the blood to clot thereby stopping the bleeding. Depending on the amount of anticoagulants that may have been administered to the patient during and prior to the procedure, the time pressure must be maintained varies from 15 minutes to more than an hour. Once bleeding has stopped, a pressure bandage is placed over the site of the puncture in an attempt to protect the integrity of the clot. The pressure bandage must remain in place for some time, usually from 8 to 24 hours. During this period of time the patient must remain in bed, sometimes requiring an overnight hospital stay.

To shorten the length of time required for the patient to become ambulatory and to lessen complications sometimes arising from the traditional method, several closure devices have been developed. One such device, as described in U.S. Pat. No. 5,620,461, a foldable sheet with an attachment thread is inserted into the opening in the blood vessel and an arresting element is applied over the attachment element against the outside of the blood vessel. Another such device is described in U.S. Pat. Nos. 6,045,569 and 6,090,130, and includes an absorbable collagen plug cinched down against an absorbable intervascular anchor via an absorbable suture. The anchor has an elongated rectangular shape that requires it to be inserted into the puncture wound with its longitudinal axis parallel to the sheath axis. This requires it to be rotated ninety degrees after insertion so that blood flow obstruction is minimized. A specially designed sheath is necessary to assure proper rotation, thus resulting in an otherwise unnecessary sheath change. The long dimension of the anchor is thus larger than the cannula inside diameter (ID) and the width is smaller than the ID. The collagen plug is in an elongated state prior to deployment and is forced into a ball shape via a slipknot in the suture, which passes through the collagen, and a tamper that applies a distal force to it. The anchor acts as a support for the suture cinch which forces the collagen ball shape up against the exterior vessel wall and the anchor. Blood flow escaping around the anchor is slowed down and absorbed by the collagen material and thus forms a clotting amalgamation outside the blood vessel that is more stable than the traditional method of a standalone clot. The added robustness of the amalgamation clot allows earlier ambulation of the patient.

The device raises several issues. It is not a true sealing device but rather a clotting enhancement device, as opposed to a device with two flat surfaces exerting sealing pressure on both the interior and exterior of the blood vessel, a much more reliable technique. In either case bleeding occurs during the time between removal of the sheath and full functionality of the deployed device. Thus "instant" sealing pressure from two flat surfaces is desirable over a method that relies to any extent on clotting time. One such device is disclosed by Bates et. al. in U.S. Pat. No. 8,080,034. The '034 device comprises an internal sealing surface pivoting on a rigid post to accommodate the longitudinal dimension of the seal inside the sheath ID. The exterior seal (second clamping member) is slidable along the rigid post and pivotal such that it, along with the internal seal, sandwiches the wall of the blood vessel via a locking ratchet. One problem with this design is that the pivoting feature increases the cross-sectional dimension of the seal thus requiring a larger diameter sheath than would be otherwise needed. In addition, the pivoting internal seal has no means to assure that the seal pivots to the correct sealing position as the ratchet closes. This could cause the internal seal to exit the blood vessel in the collapsed configuration as the user withdraws the deploying device.

The seals are release by the user cutting the suture thread in the device described in U.S. Pat. No. 6,045,569.

It is known that the opening in the blood vessel closes to some extent after the sheath is removed thus allowing smaller seal surfaces than would otherwise be required. What is less known is that the opening does not close as quickly as a truly elastic material such as natural rubber. For this reason seal surfaces of closure devices that are activated in less than a second, or perhaps even longer, after sheath removal must be physically larger than the sheath outside diameter to avoid embolization of the seals because of the delayed vessel closure. The design of seals that are deployed through a sheath ID with dimensions larger than the sheath OD upon deployment is a challenge since the preferred material for seals are bio-absorbable and thus have limited mechanical properties.

The '569 device requires removing the catheter sheath and replacing it with a custom sheath prior to deployment, resulting in addition blood loss. The tamping force used to deploy the collagen against the anchor is left to the surgeon's feel sometimes resulting in inadequate deployment and other times resulting in the collagen being pushed through the puncture wound, into the blood vessel along with the anchor. Inadequate tamping results in excessive bleeding with the potential for painful hematoma and over tamping can result in a surgical procedure to remove the device from the blood vessel lumen. In addition, the absorption rate of the suture, the collagen, and the anchor may be different owing to the fact that they are formed from different materials, sometimes resulting in the detachment of the anchor, which can move freely in the blood stream and become lodged in the lower extremities of the body, again requiring surgical removal.

It is worth noting that the prior art device, U.S. Pat. No. 6,045,569, relies on clotting and is not a true vessel seal. U.S. patent application 20060265007 discloses an automatic tamping system that is usable on devices such as those described in U.S. Pat. Nos. 6,045,569 and 6,090,130, to automate certain aspects of deployment but it fails to provide a means for detecting the artery wall. Automatically deployment requires detection of the seal against the artery wall to avoid early deployment and potential embolization. The lack of such automation can cause deployment errors that result in bleeding and other serious events. In addition the '569 device requires 11 steps to complete hemostasis requiring 4-10 minutes of valuable facility and staff time.

It would be desirable therefore to provide a vessel-sealing device that actually seals the blood vessel and does not rely on the clotting of the blood. It is also desirable to provide a closure device that is deployable through the catheter sheath with minimal steps requiring less than 2 minutes for hemostasis. It would be also desirable to provide a reliable vessel-sealing device the deployment efficacy of which is independent of the surgeon's feel, i.e. automatic deployment and automatic release of the seals from the deployment instrument.

SUMMARY OF THE INVENTION

The present invention is directed to a device for sealing an opening in the wall of a blood vessel, the blood vessel having an interior wall surface, exterior wall surface, and a lumen, the device includes an automatic mechanism, a shaft extending between a proximal end and a distal end, the shaft being fixedly connected to the automatic mechanism, a seal assembly having a first portion and a second portion, the seal assembly operatively attached at the first portion to the distal end of the shaft, the seal assembly configured to engage the interior wall surface and the exterior wall surface of the blood vessel, and a pushing rod operatively engaging the seal assembly at the second portion and movable relative to the shaft, the automatic mechanism moving the pushing rod from a first position to a second position in response to the shaft being pulled distally a predetermined distance.

In some embodiments, the device also includes a safety latch, the safety latch movable between a first position and a second position, the safety latch engaging a pusher of the automatic mechanism in the first position thereby preventing the pusher from moving the pushing rod.

In some embodiments, the automatic mechanism includes a pusher, the pusher moving the pushing rod from a first position to a second position in response to the shaft being pulled distally a predetermined distance.

In some embodiments, the automatic mechanism includes a shaft retaining element fixedly attached to the shaft, a pusher, the pusher fixedly attached to the pushing rod, a spring, a spring retainer, the spring biased against at least one surface of the spring retainer, and at least one retention element rotatably movable between a first and second position, the at least one retention element disposed adjacent the spring retainer and engages the spring retainer in the first position.

In some embodiments, the shaft pulls the shaft retaining element distally, allowing the spring retainer to rotate the at least one retaining element and engage the pusher to move the pusher distally.

The present invention is also directed to a device for sealing an opening in the wall of a blood vessel, the blood vessel having an interior wall surface, exterior wall surface, and a lumen, the device includes an automatic mechanism comprising a shaft retaining element, a pusher, a spring retainer, a spring biased against at least one surface of the spring retainer, at least one retention element rotatably movable between a first and second position, the at least one retention element disposed adjacent the spring retainer and engages the spring retainer in the first position, a shaft extending between a proximal end and a distal end, the shaft being fixedly connected to the shaft retaining element, a seal assembly having a first portion and a second portion, the seal assembly operatively attached at the first portion to the distal end of the shaft, the seal assembly configured to engage the interior wall surface and the exterior wall surface of the blood vessel, and a pushing rod fixedly attached to the pusher and movable relative to the shaft, the pushing rod operatively engaging the seal assembly at the second portion, the pusher moving the pushing rod from a first position to a second position in response to the shaft being pulled distally a predetermined distance.

In yet another aspect, the present invention is directed to a method of sealing an opening in the wall of a blood vessel, the blood vessel having an interior wall surface, exterior wall surface, and a lumen, the method includes inserting at least a portion of a distal end of an automatic device through the opening and into the lumen, the distal end having a seal assembly that includes a first sealing element disposed in the lumen of the blood vessel and configured to engage the interior wall surface and a second sealing element to engage the exterior wall surface, pulling proximally on the automatic device, causing the first sealing element to engage the interior wall surface and pull on a shaft connected to the seal assembly, thereby causing the automatic device to automatically push the second sealing element against the exterior wall surface sealing the opening in the wall of the blood vessel, and removing automatic device leaving only the seal assembly behind.

Additional features and advantages of the invention will be set forth in the detailed description which follows, and in part will be readily apparent to those skilled in the art from that description or recognized by practicing the invention as described herein, including the detailed description which follows, the claims, as well as the appended drawings.

It is to be understood that both the foregoing general description and the following detailed description of the present embodiments of the invention, and are intended to provide an overview or framework for understanding the nature and character of the invention as it is claimed. The accompanying drawings are included to provide a further understanding of the invention, and are incorporated into and constitute a part of this specification. The drawings illustrate various embodiments of the invention and together with the description serve to explain the principles and operations of the invention.

BRIEF DESCRIPTION OF THE DRAWINGS

FIG. 7 is a front perspective view of the sealing device with the top handle half removed;

FIG. 8 is a perspective partial view of the safety latch;

DETAILED DESCRIPTION OF THE PREFERRED EMBODIMENTS

Figure 1:
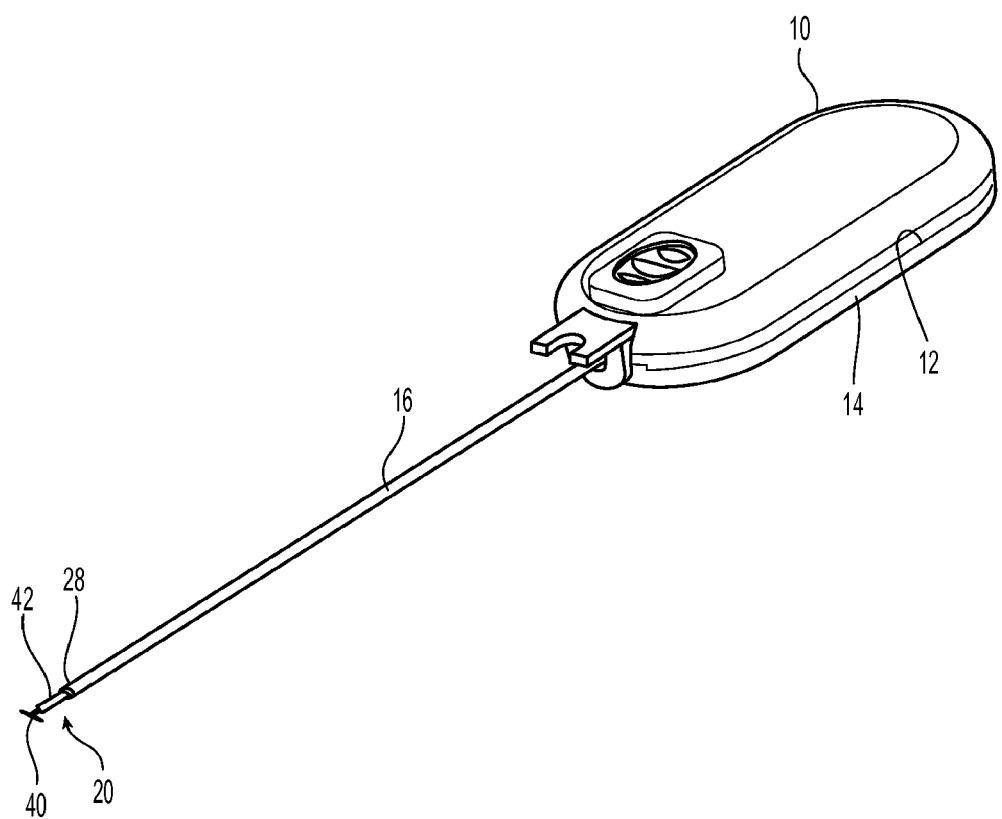
FIG. 1 is a perspective view of one embodiment of a sealing device according to the present invention.

Reference will now be made in detail to the present preferred embodiment(s) of the invention, examples of which are illustrated in the accompanying drawings. Whenever possible, the same reference numerals will be used throughout the drawings to refer to the same or like parts.

Figure 2:
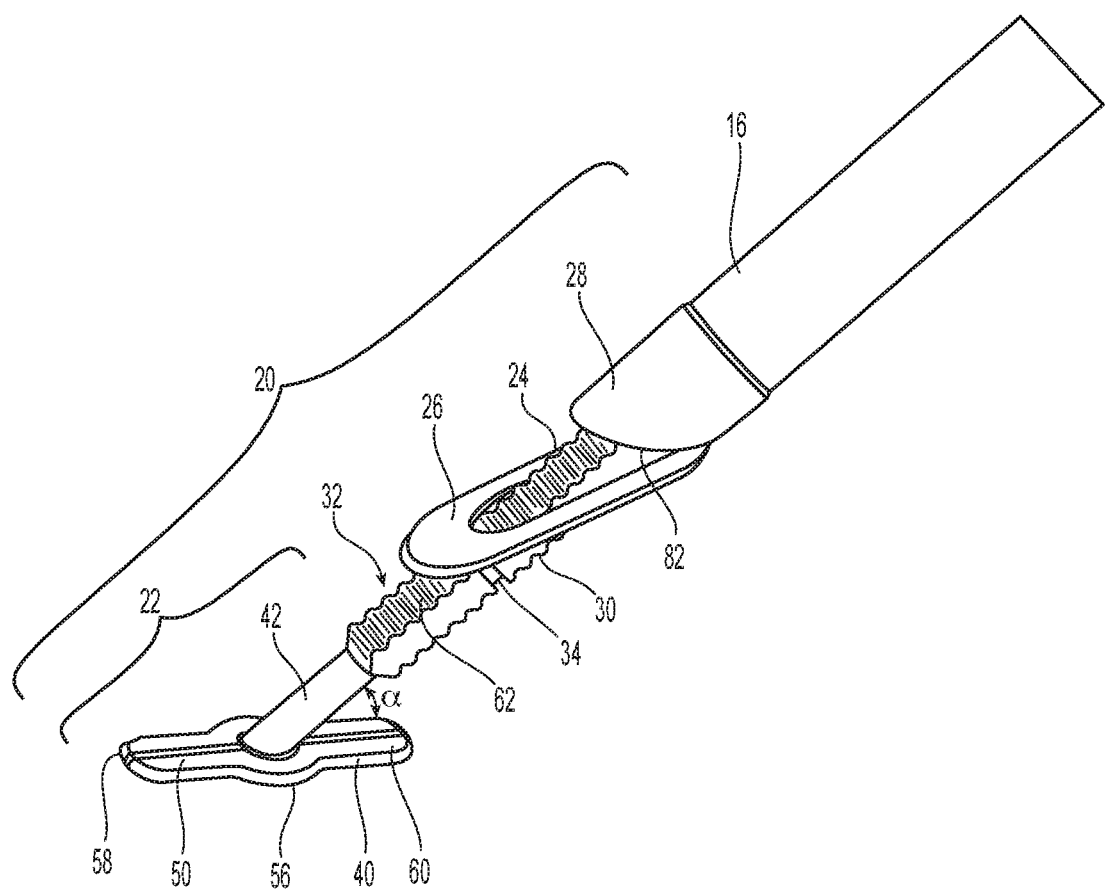
FIG. 2 is a perspective view of a portion of the sealing device of FIG. 1 illustrating the seal assembly thereof.
Figure 15:
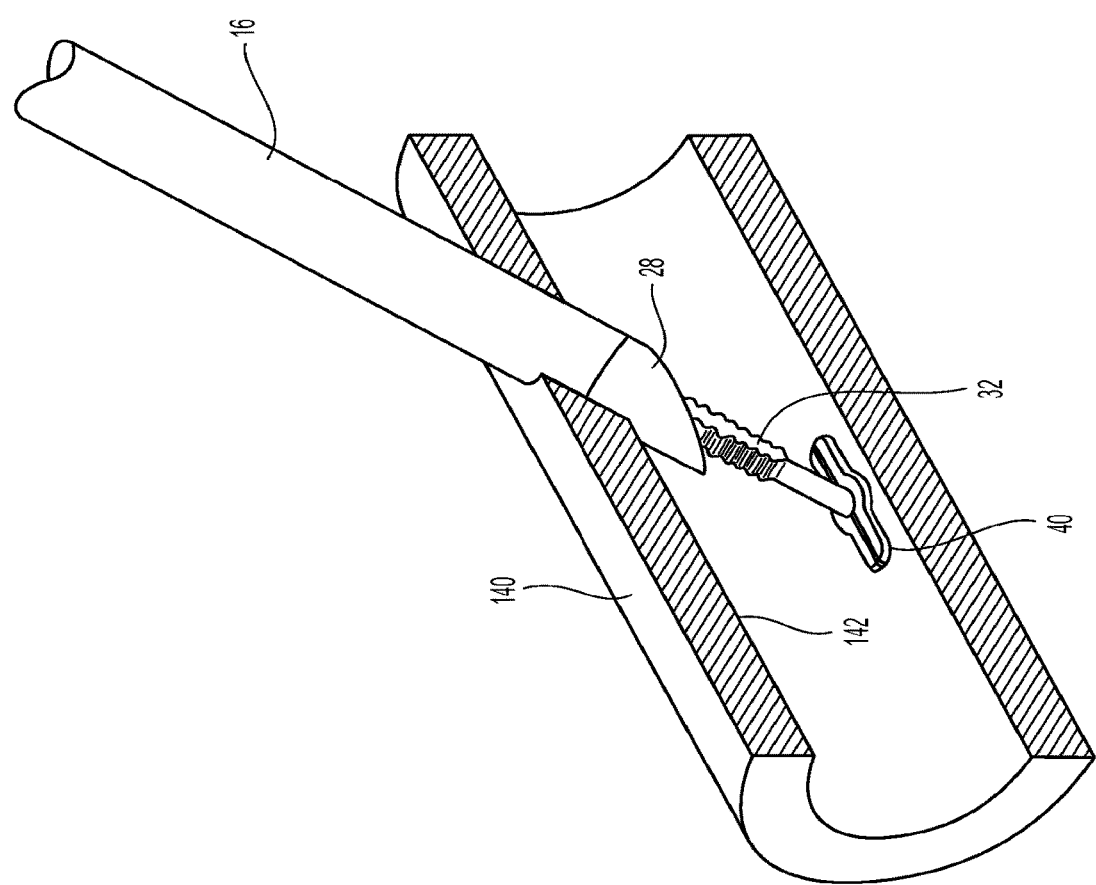
FIG. 15 is partial cross section view of a blood vessel with the sealing device inserted therein.
Figure 16:
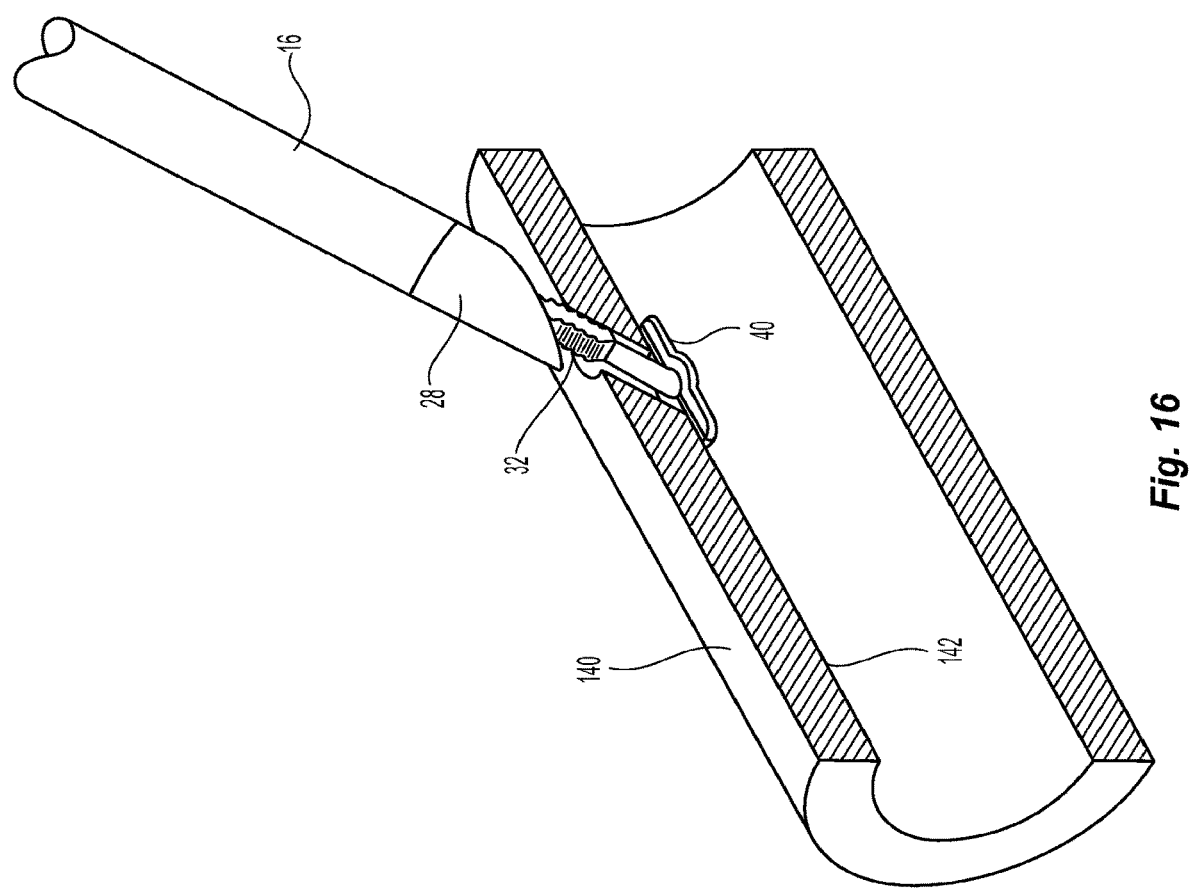
FIG. 16 is perspective view of the sealing device inserted into the blood vessel just before the sealing device is activated.

Referring to FIGS. 1 and 2, closure device 10 is illustrated as having two handle halves 12,14 that house an automatic mechanism, described in more detail below, which is coupled to the seal assembly 20 by a flexible pusher rod 16 and a flexible shaft 18. See FIG. 6. The seal assembly will be described briefly here, but is the subject of co-pending application titled "Improved Vessel Seal Device," assigned Ser. No. 13/746,278, the contents of which are incorporated herein by reference in their entirety. Seal assembly 20 has a first sealing element 22, a knobbed rigid shaft 24, an outer floating element 26, and a second sealing element 28. Knobbed, rigid shaft 24 has a proximal section 30 and a distal section 32 separated by a weakened notch feature 34, which is configured to separate seal assembly 20 from the rest of the closure device 10 once the automatic deployment and sealing process is complete. The length of the distal section 32 of knobbed shaft 24 is dictated by the thickness of the blood vessel wall that can be accommodated. See FIG. 15. The first sealing element 22 also has a distal section 40 configured to interface with the inside wall of a vessel to be sealed, a knobbed, rigid distal shaft section 32 (which is a part of the knobbed, rigid shaft 24), and ankle section 42 joining the distal section 40 to the knobbed, rigid distal shaft section 32. The ankle section 42 is attached to distal section 40 at an angle α, which is preferably at an angle of about 45°. Although other angles may be used, the value of angle α may cause other values of the seal assembly to be changed, as discussed in detail below.

Figure 3A:
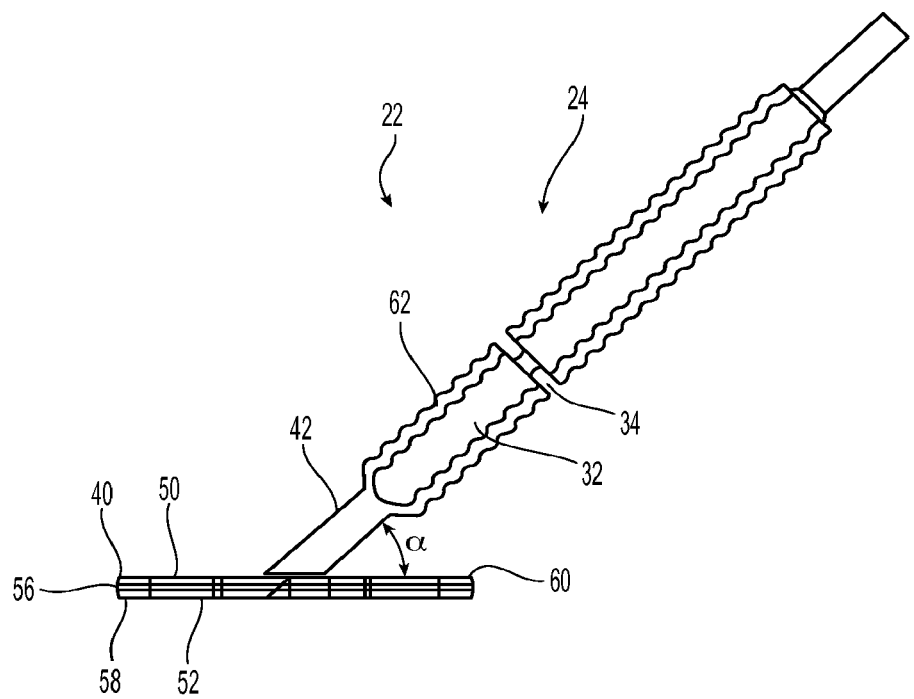
FIG. 3A is a side plan view of the first sealing element and the shaft.
Figure 3B:
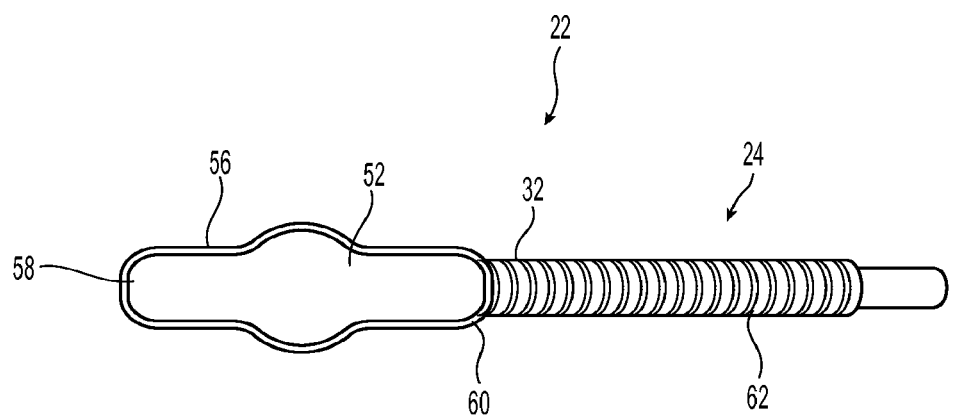
FIG. 3B is a bottom plan view of the first sealing element and the shaft.

More detailed views of the first sealing element 22 and the knobbed rigid shaft 24 are illustrated in FIGS. 3A-3B. The first sealing element 22 has the distal section 40, ankle section 42 and the knobbed, rigid distal shaft section 32. The distal section 40 has a proximal or top surface 50, a bottom surface 52 and an outer peripheral surface 56. The proximal or top surface 50 is preferably configured to engage the interior wall surface 142 of the blood vessel 140 (see FIG. 15), which means that the top surface 50 is preferably flat. However, the top surface 50 can be of any configuration (e.g., flat, convex, etc) and still come within the scope of the present invention. The bottom surface 52 is preferably flat, but may have other configurations. As noted below, the exact configuration of the surfaces 50,52 may also depend on the strain that is placed on them prior to and during insertion. The outer peripheral surface 56 is preferably continuous in that it has no discontinuities. That is, the outer peripheral surface 56 is smooth and has no sharp angles (e.g., 30, 45 or 90° angles). Since the distal section 40 is to be deformed prior to insertion into the blood vessel 140, any sharp angles tend to create stress points, potentially causing the distal section 40 to be bent/deflected beyond its ability to return to its original configuration. The distal section 40 has a thickness that increases from the front (or distal) end 58 to the rear (or proximal) end 60. In the embodiment illustrated in the figures, the thickness increases from 0.28 mm at the front end 58 to 0.30 mm at the rear end 60. However, other thicknesses and tapered shapes fall within the scope of the present invention.

Figure 4B:
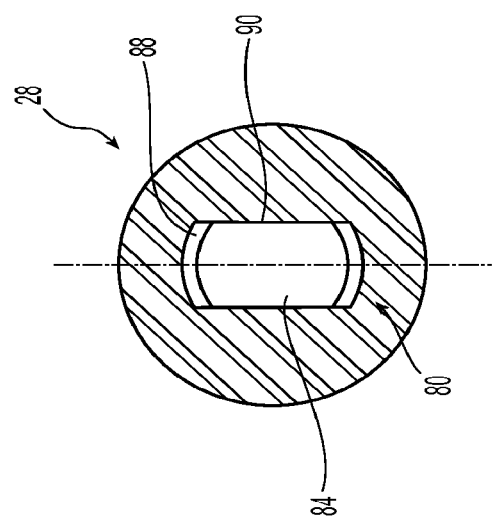
FIG. 4B is a cross section view of the second sealing element of the seal assembly of FIG. 2 that is orthogonal to the view in FIG. 2.
Figure 4A:
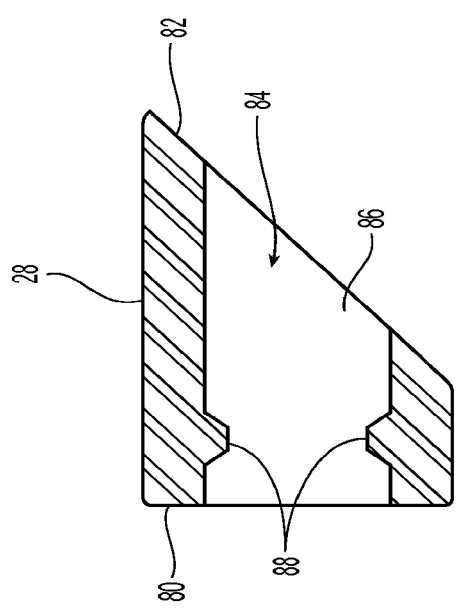
FIG. 4A is a cross section view along a longitudinal axis of a second sealing element of the seal assembly of FIG. 2.

Second sealing element 28 is shown in more detail in FIGS. 4A and 4B. The second sealing element 28 has a proximally facing surface 80 and a sloped distally facing surface 82. An internal opening 84 defined by the internal surface 86 extends between the proximally facing surface 80 and the sloped distally facing surface 82. The internal surface 86 has extending therefrom and into the internal opening 84 projections 88 that interface with and engage the knobs 62 with an interference fit such that second sealing element 28 and knobbed rigid shaft 24 function as a one way latch assuring an adequate compression force regardless of the blood vessel wall thickness.

The internal opening 84 of second sealing element 28 (and floating foot 26) have two flat surfaces 90 on opposite sides of the internal opening 84 that interface with flat surfaces 68,70 of knobbed rigid shaft 24 to provide rotational stability of the seal assembly components 26,28 thus assuring that the sloped distally facing surface 82 and the fully deployed floating foot 26 remain parallel with the distal section 40 of the first sealing element 22 and the proximal or top surface 50 in particular.

Figure 5A:
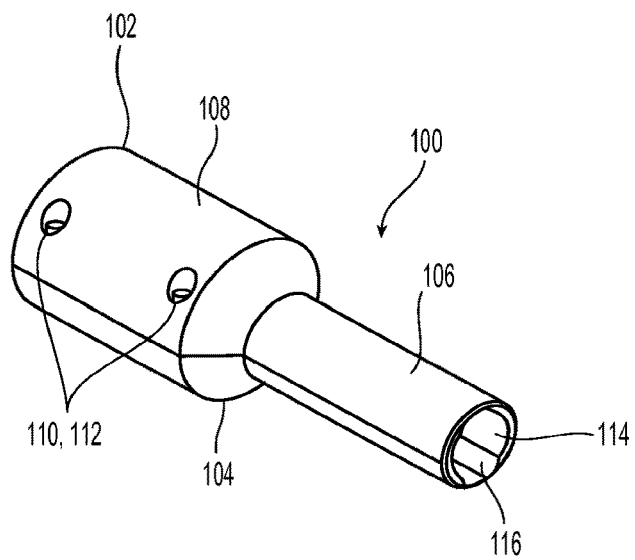
FIG. 5A is a perspective view of a sheath introducer used with the sealing device of FIG. 1.
Figure 5B:
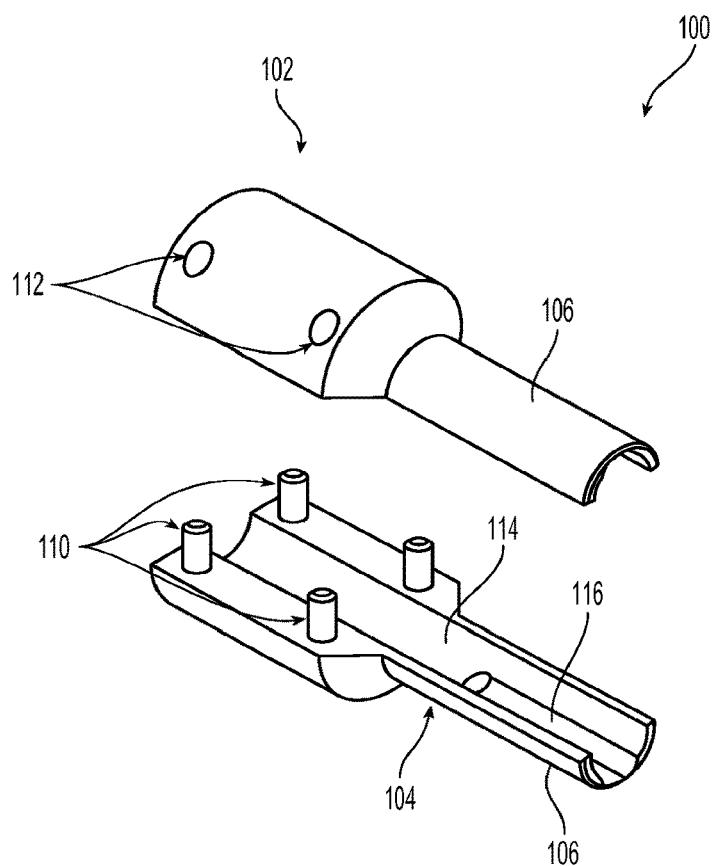
FIG. 5B is an exploded, perspective view of the sheath introducer of FIG. 5A.

FIGS. 5A and 6B depict introducer or outer sleeve 100, which is configured to protect seal assembly 20 from damage when inserting seal assembly 20 through a hemostatic valve, which, as discussed below and in more detail in the co-pending application, is one method in which the seal assembly is inserted into the patient. Introducer 100 comprises two halves, 102,104, which when assembled together form a generally cylindrical body having two different diameters. Front section 106 of introducer 100 has a smaller diameter than rear section 108. Front section 106 with the smaller diameter is configured to be inserted into hemostatic valve and rear section 108, having the larger diameter remains proximal to the hemostatic valve. While the two halves 102,104 can be assembled according to any typical manner, pins 110 on one of the two halves 102,104 are configured with a press fit into corresponding mating holes 112 thus holding halves 102,104 firmly together.

Figure 6:
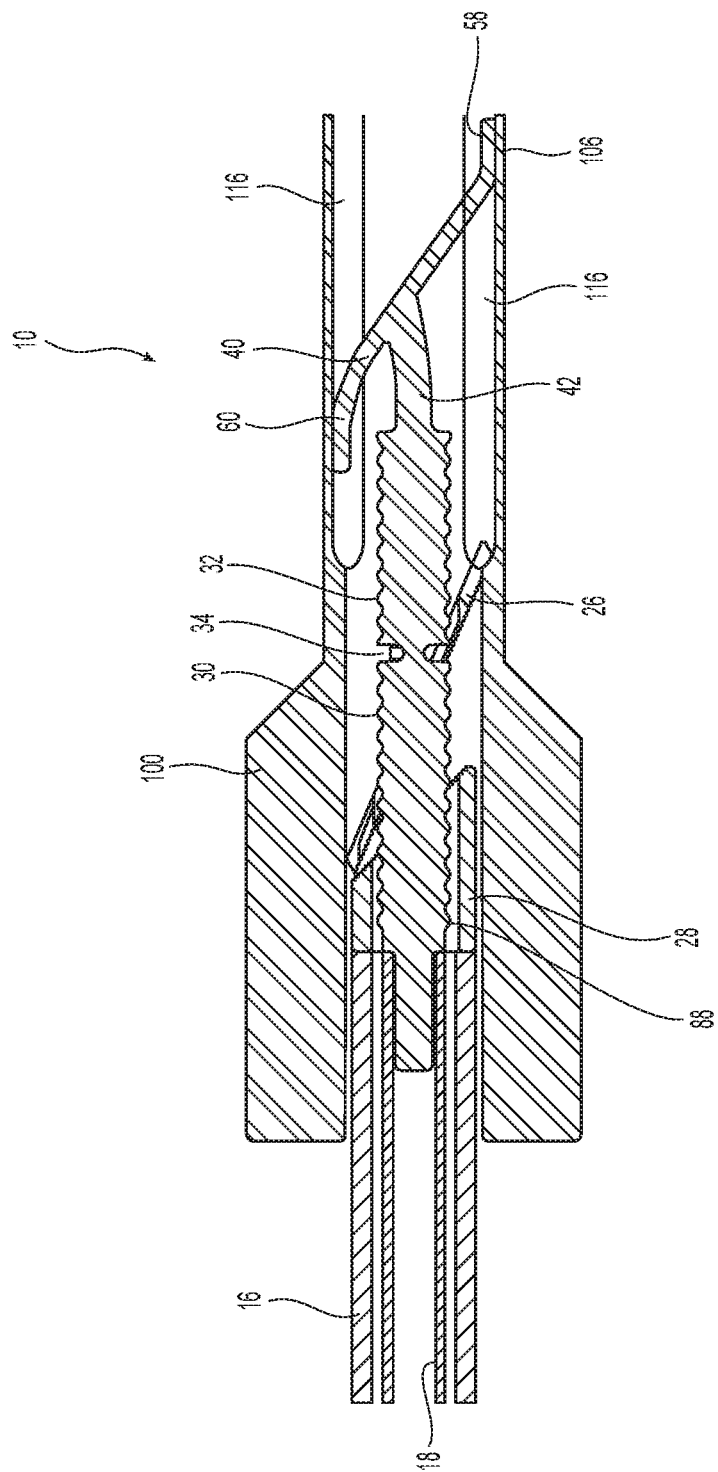
FIG. 6 is a cross section view of the seal assembly constrained in a sheath introducer.
Figure 9:
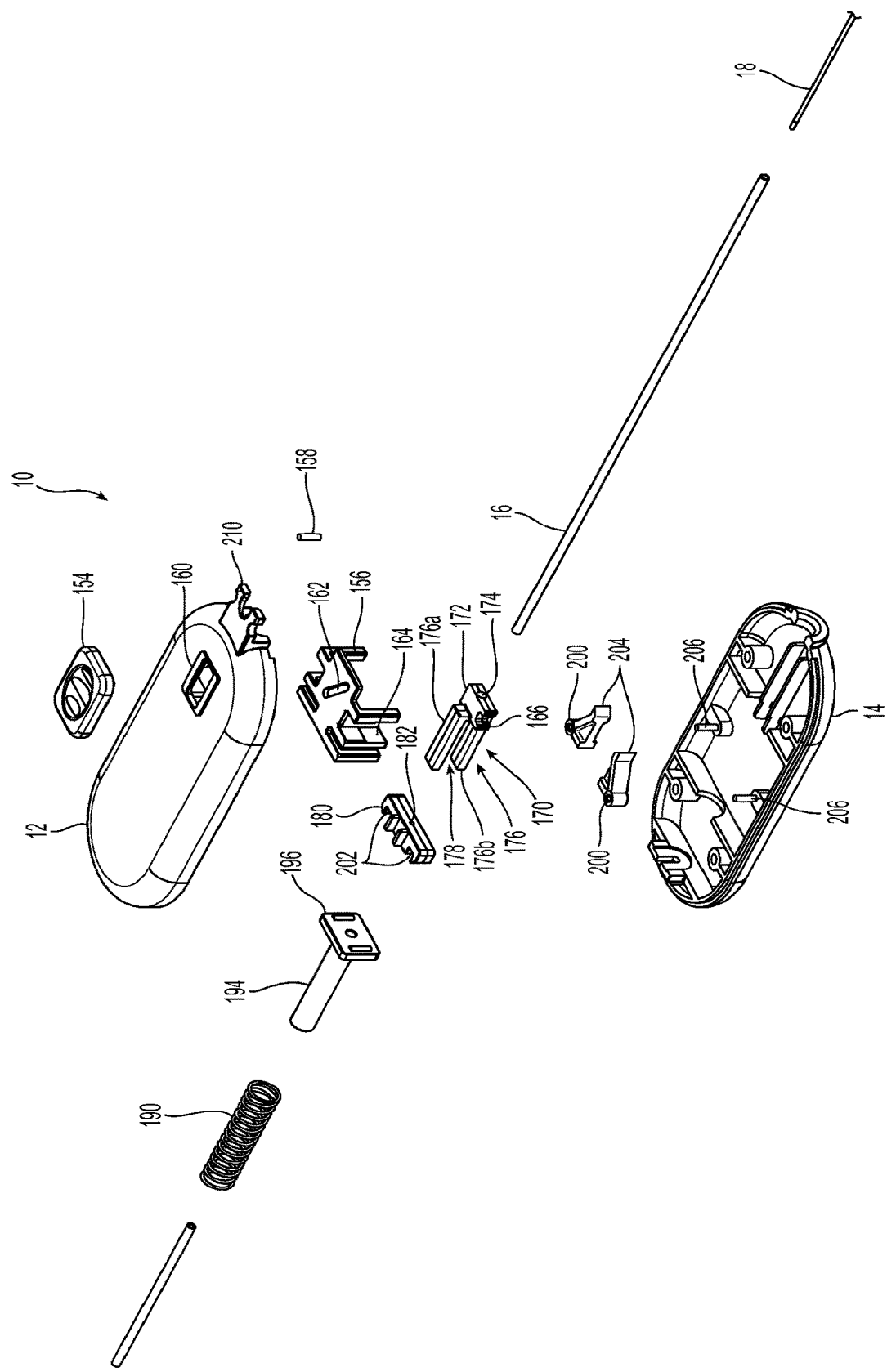
FIG. 9 is an exploded view of the sealing device of FIG. 1.
Figure 10:
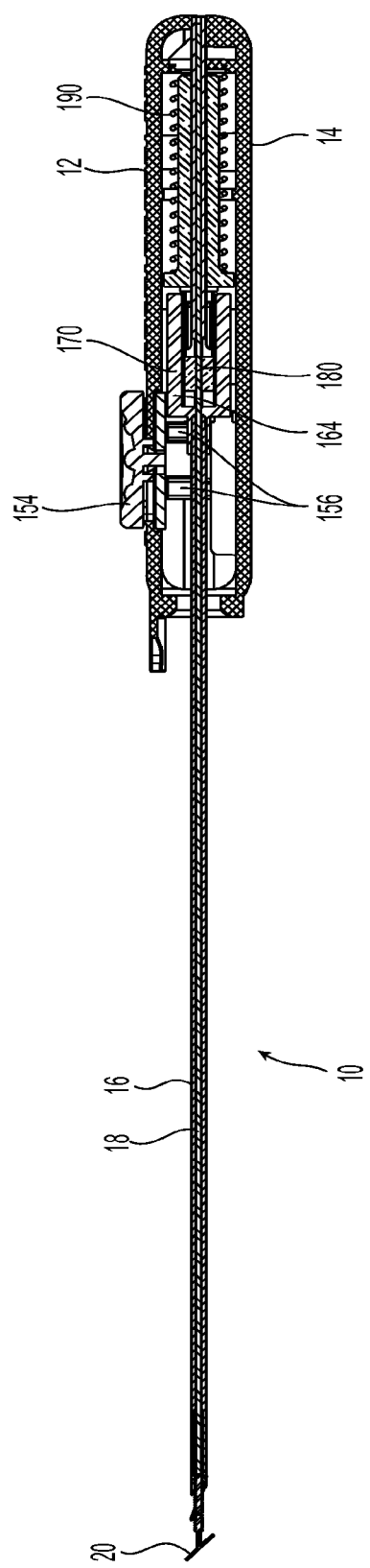
FIG. 10 is a cross section view of the sealing device of FIG. 1 along the longitudinal axis.
Figure 11:
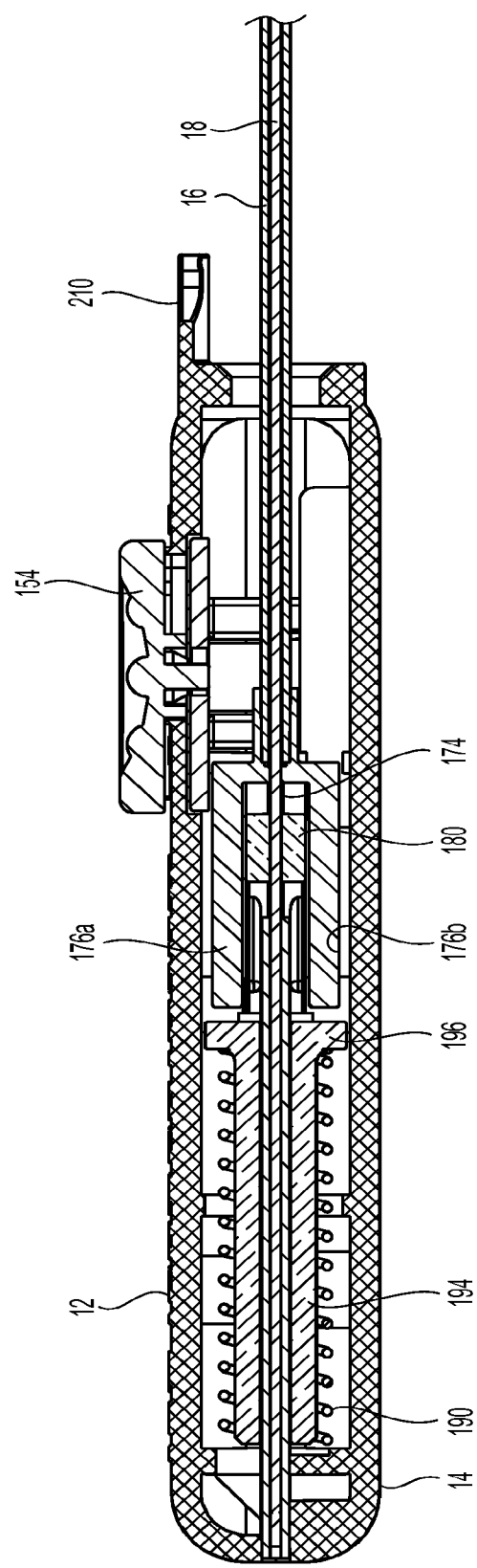
FIG. 11 is an enlarged, partial cross section view of the sealing device of FIG. 1.

The introducer 100 has an opening 114 that extends between the front section 106 and the rear section 108. However, within the opening 114 are also grooves 116 that are configured to accept seal assembly 20. The opening 114 is also configured to receive at least a portion of pusher 16 of the seal device 10. FIG. 6 is a cross section of seal assembly 20 in the initial position inside introducer 100 prior to insertion into a sheath 120. See FIG. 6. The front end 58 and the rear end 60 of the distal portion 40 of first sealing element 22 are deformed into a configuration such that the distal portion 40 of first sealing element 22 is able to pass through the inside dimension of cannula 122 upon insertion of closure device 10 resulting in the configuration shown in FIG. 6. After exit from distal end of cannula 122, the front end 58 and the rear end 60 of the distal portion 40 of first sealing element 22 return to the initial configuration as shown in FIG. 2 owing to the configuration shown in FIG. 6 not exceeding the elastic limit of the material from which the seal assembly 20 is constructed.

Turning now to the main portion of the closure device 10 and referring to FIGS. 7-13, closure device 10 comprises two handle halves 12, 14 that housing automatic mechanism 150. The automatic mechanism 150 interfaces with safety latch 152, which has a safety slide 154 that interacts with safety cage 156 via pin 158. The safety latch 152 operates such that with safety slide 154 in the distal most position automatic mechanism 150 cannot be activated. The proximal most position of safety slide 154 allows automatic activation, explained in more detail below. The pin 158 is in the center of the underside of safety slide 154 and passes through handle opening 160 of handle half 12 and engages slot 162 of safety cage 156. With the safety slide 154 in the full distal position, the pin 158 forces safety cage 156 into the position shown in FIG. 7 (to the left looking distally) such that leg 164 is forced into a slot 166 in pusher 170 that locks the movable pusher 170 against distal movement. The movement of the other parts of the automatic mechanism 150 are discussed in more detail below. In this position, safety slide 154 covers the word "READY" (or any other word, mark or appropriate indicia) and exposes the word "SAFE" (or any other word, mark or appropriate indicia) embossed on handle half 12. In this position, the safety latch 152 prevents the automatic mechanism 150 from premature firing during shipment or handling. With safety slide 154 in the proximal-most position, the pin 158 forces safety slide 154 to the right, thus removing leg 164 from the slot 166 in pusher 170. In this position the automatic mechanism 150 is free to initiate when first sealing element 22 interacts with the inside of vessel wall 142. In this configuration safety slide 154 covers the word "SAFE" and exposes the word "READY" on handle half 12.

Flexible pusher rod 16 is a cannulated cylinder, the proximal end of which is connected by an adhesive or by another appropriate method to the movable pusher 170. The movable pusher 170 has a front portion 172 with an opening 174 for engagement with the flexible pusher rod 16 and to allow the flexible shaft 18 to pass through front portion 172. The pusher 170 also has a rear portion 176 that is divided into an upper portion 176a and a lower portion 176b, the upper portion 176a and a lower portion 176b defining an opening 178 therebetween.

The automatic mechanism 150 also includes a shaft retaining element 180 that, in the initial or preactivation stage, is disposed in opening 178 defined by the upper portion 176a and a lower portion 176b of pusher 170. The shaft retaining element 180 also has an opening 182 passing therethrough to allow the flexible shaft 18 to pass therethrough and extend proximally in the automatic mechanism 150. However, the flexible shaft 18 is fixedly attached to the shaft retaining element 180. The flexible shaft 18 therefore extends almost the entire length of the device 10. As noted above, the flexible shaft 18 is also connected to the knobbed rigid shaft 24 of the seal assembly 20. As explained below, a tensile force on the flexible shaft 18 causes the automatic mechanism 150 to fire.

The automatic mechanism 150 also has a spring 190, which is illustrated as a cylindrical spring, but could be any resilient element and have any configuration. The spring 190 engages, at its proximal end, the proximal end of the handle 12,14. The spring 190 is disposed around a spring retainer 194 and engages at its distal end, the front end 196 of the spring retainer 194. The spring 190 is biased against the front end 196 of the spring retainer 194 to push the spring retainer 194 against the pusher 170, as described in more detail below.

The automatic mechanism 150 also has two retention elements 200 that are rotatably mounted in the housing 12,14. The two retention elements 200 are illustrated as being generally triangular, but could be of any shape or configuration as long as they perform the functions noted below. The retention elements 200 are disposed to engage the front end 196 of the spring retainer 194 and the shaft retaining element 180. In fact, each of the two retention elements 200 engage a notch 202 on either side of the shaft retaining element 180. The retention elements 200 each have an end portion 204, preferably a flat surface, that engages an internal surface of the notches 202. As can best be seen in FIG. 9, the retention elements 200 are disposed on round projections 206 extending upward from the handle 14. The projections 206 could also project downward from the handle 12.

Figure 12:
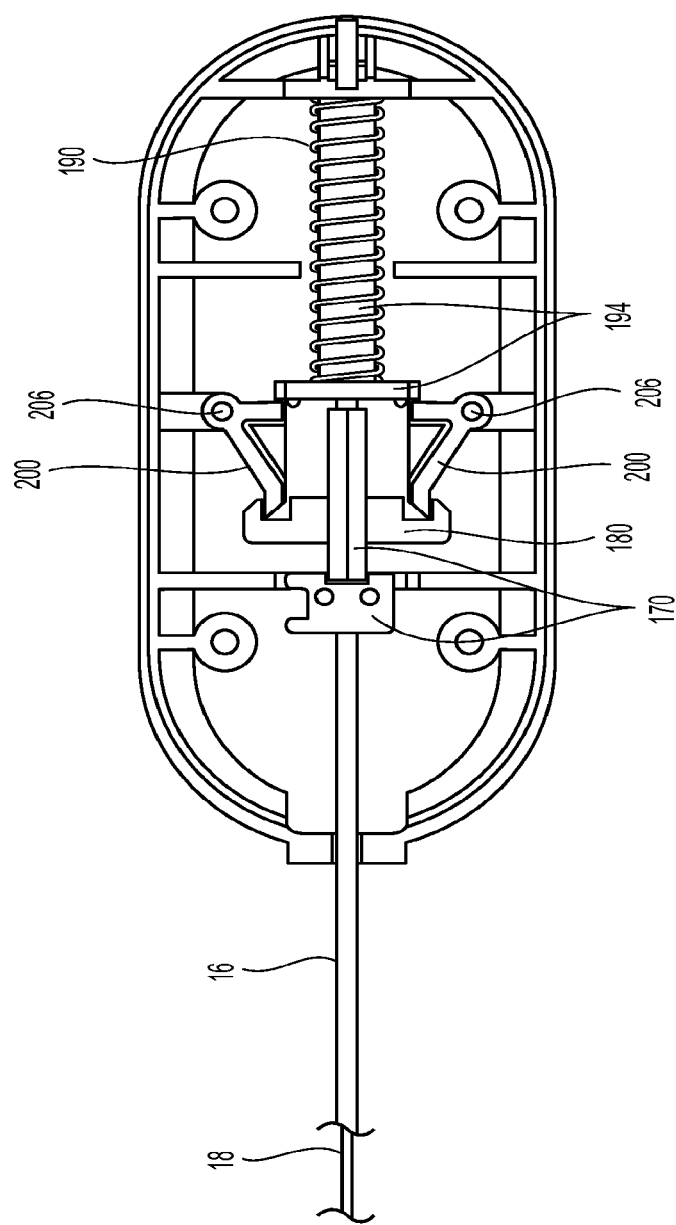
FIG. 12 is a top view of the sealing device of FIG. 1 with the top half of the handle and safety latch removed in a pre-insertion configuration.
Figure 13:
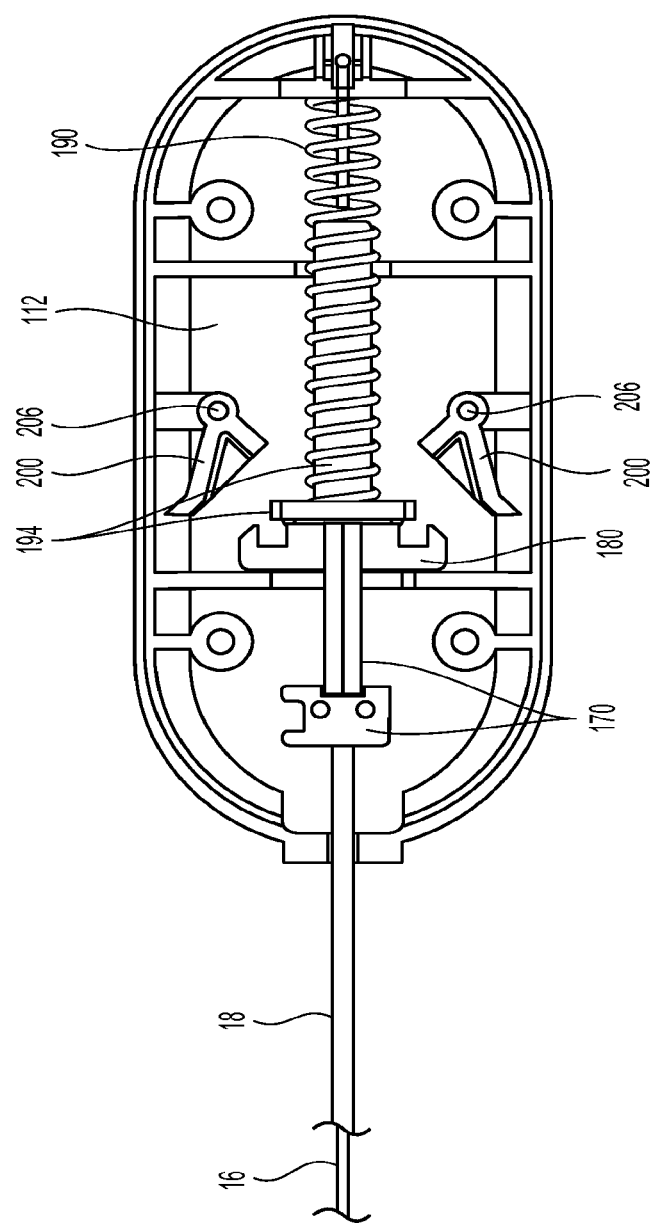
FIG. 13 is a top view of the sealing device of FIG. 1 with the top half of the handle and safety latch removed in a post-firing configuration.
Figure 14:
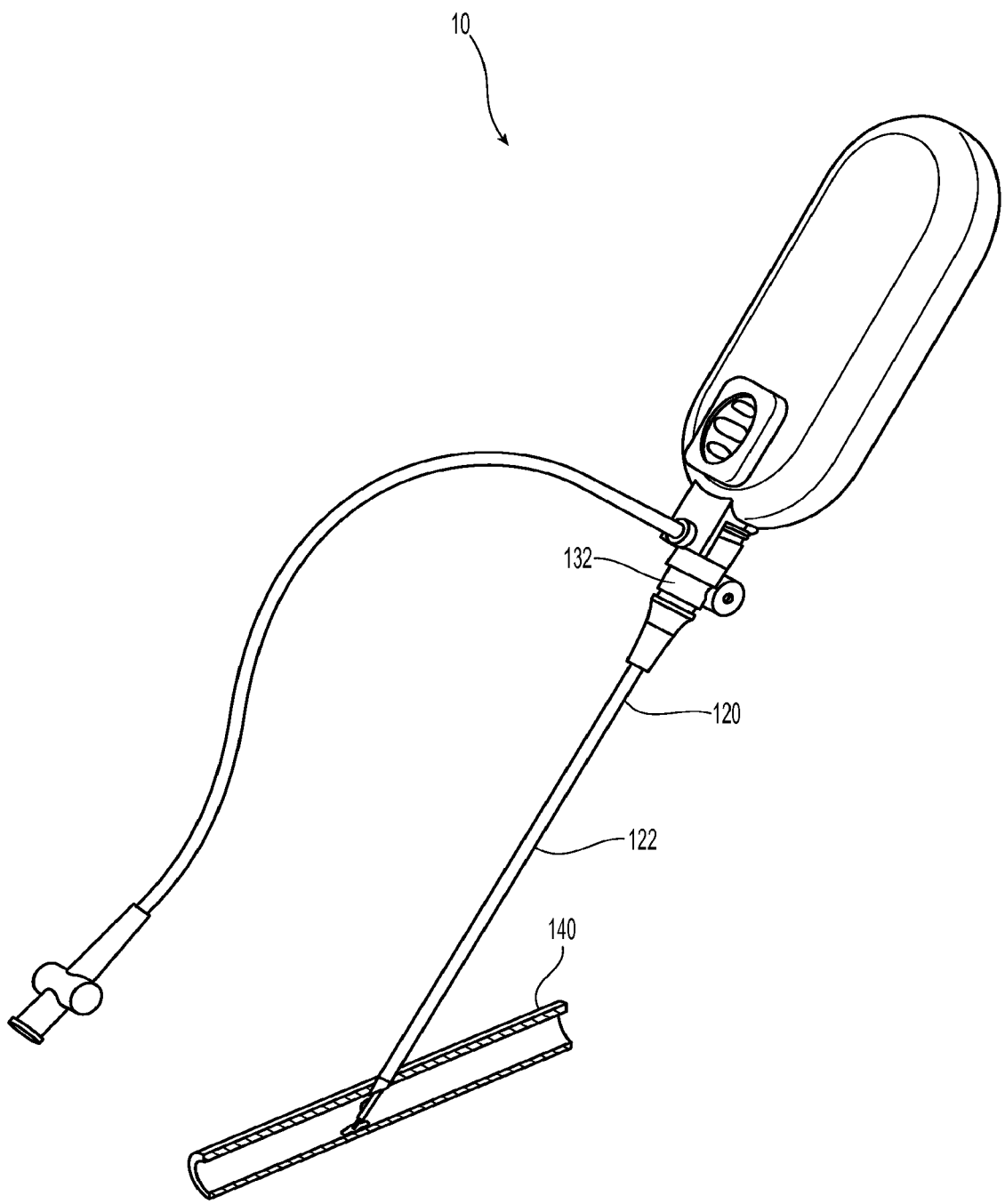
FIG. 14 is a perspective view of the sealing device inserted into a blood vessel.

The use of the device 10 will now be described in conjunction with FIGS. 12-17. FIGS. 12 and 13 are top views of the device with the upper handle half 12 and the safety latch 152 removed for clarity and to show pre-firing and post-firing, respectively. In FIG. 12, the spring 190 is compressed by spring retainer 194, which when released will provide the kinetic energy to seal the opening in the blood vessel and to break the knobbed rigid shaft 24. The spring retainer 194, and in particular the front end 196, is biased against the retention elements 200. The retention elements 200 can not move due to the end portion 204 engaging the internal surface of the notches 202 of the shaft retaining element 180. The front end 196 of spring retainer 194 is separated from the pusher 170 by the retention elements 200. Keeping in mind that the shaft retaining element 180 is secured to the flexible shaft 18, which in turn is secured to the knobbed rigid shaft 24, pulling on the seal assembly 20 will cause the flexible shaft 18 to be pulled distally and move shaft retaining element 180 distally as well. This allows the retention elements 200 to rotate outward given the biasing of the front end 196 of the spring retainer 194. The front end 196 of the spring retainer 194 can then push pusher 170 connected to the flexible pusher rod 16 distally. The effect of this movement is illustrated in FIG. 13.

Figure 17:
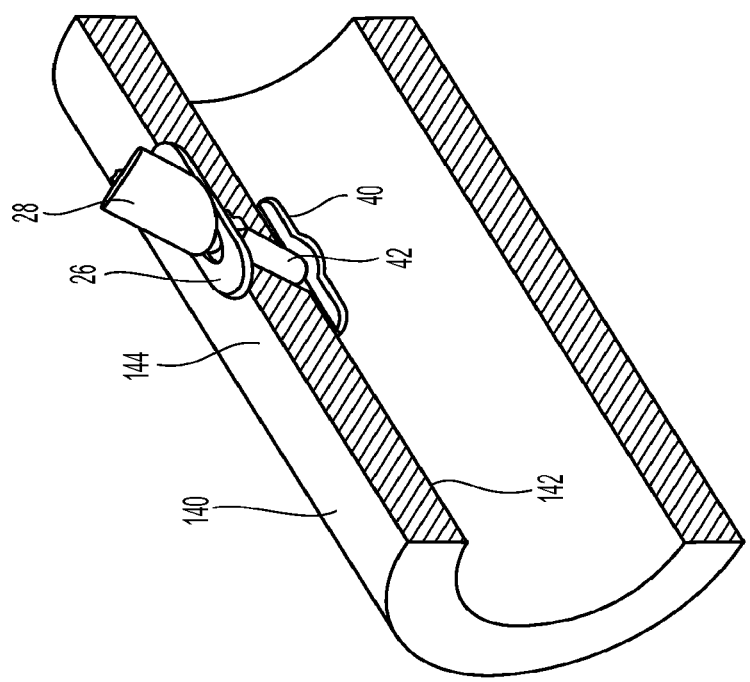
FIG. 17 is a perspective view of the seal assembly blocking the opening in the blood vessel after activation of the sealing device.

A method of using the current invention in conjunction with FIGS. 14-17 is as follows: The device 10, and in particular the seal assembly 20 is inserted into sheath introducer 100 that surrounds and deforms seal assembly 20 such that seal assembly seal 20 can pass through sheath valve 132. See also FIG. 6. The device 10 and sheath introducer 100 is inserted into a hemostatic valve for insertion into the patient. The device 10 preferably has a latch 210 that can be used to attach the device 10 to the sheath 120. This allows for the simultaneous removal of the device 10 and the sheath 120, if the sheath is not removed prior to the activation of the automatic mechanism 150. Inserting pusher 16 through sheath 120, including valve 132 and cannula 122, causes at least a portion of seal assembly 20 to exit the distal end of cannula 122 and into blood vessel 140. See FIG. 14. A portion of the second sealing element 28 and the pusher 16 may be disposed within the blood vessel 140. See FIG. 15. The sheath 120 may then be removed from the device 10. Pulling on the closure device 10, the proximal or top surface 50 of the distal portion 40 of first sealing element 22 engages the interior blood vessel wall 142. See FIG. 16. This would also remove the second sealing element 28, the outer floating element 26, and the pusher 16 from within the blood vessel 140. Continuing to pull on the sealing assembly 20 and therefore flexible shaft 18 triggers the automatic mechanism 150 in the closure device 10, which pushes pusher 16, and which in turn pushes second sealing element 28, and floating foot 26 distally such that floating foot 26 is in contact with outer wall 144 of blood vessel 140. This will sandwich the second sealing element 28 against floating foot 26, blood vessel 140 and distal portion 40 of first sealing element 22 such that the opening in blood vessel 140 is hemostatically sealed, as shown in FIG. 17.

The initial spring compression is chosen such that accounting for friction losses the remaining kinetic energy is sufficient to break weakened notch feature 34 of knobbed rigid shaft 24 resulting in the distal truncated portion of seal assembly 20 becoming detached from the rest of closure device 10 and also providing vessel hemostasis as shown in FIG. 17. Note that as the user moves sheath 120 and closure device 10 proximally activating the automatic process and removes the two latched components, the handle and the sheath, from the body nothing remains in the patient except the bio-absorbable truncated portion of seal assembly 20. Thus the entire closure process of sealing and disconnection is automatic requiring no "tactical feel" of the user.

It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

I claim:

1. A device for sealing an opening in the wall of a blood vessel, the blood vessel having an interior wall surface, an exterior wall surface, and a lumen, the device comprising:
    a pushing rod, the pushing rod having an opening therealong;
    a shaft disposed within at least a portion of the opening of the pushing rod;
    a shaft retaining element fixedly attached to the shaft;
    a pusher, the pusher fixedly attached to the pushing rod;
    a spring;
    a spring retainer, the spring biased against at least one surface of the spring retainer; and
    at least one retention element rotatably movable between a first and a second position, the at least one retention element engages the spring retainer and the shaft retaining element in the first position; and
    a seal assembly having a first portion and a second portion, the seal assembly operatively attached at the first portion to the distal end of the shaft, the seal assembly configured to engage the interior wall surface and the exterior wall surface of the blood vessel,
    wherein the pushing rod operatively engages the seal assembly at the second portion and is movable relative to the shaft, the pushing rod moving from a first position to a second position in response to the shaft moving distally causing the first portion and the second portion of the seal assembly to move relative to one another.

2. The device for sealing an opening according to claim 1, wherein the at least one retention element comprises two retention elements.

3. The device for sealing an opening according to claim 1, wherein the at least one retention element has two legs, a first leg engaging the spring retainer and a second leg engaging the shaft retaining element.

4. The device for sealing an opening according to claim 3, wherein the second leg is longer than the first leg.

5. The device for sealing an opening according to claim 1, further comprising a safety latch, the safety latch movable between a first position and a second position, the safety latch engaging a slot in the pusher thereby preventing the pusher from moving the pushing rod.

6. A device for sealing an opening in the wall of a blood vessel, the blood vessel having an interior wall surface, an exterior wall surface, and a lumen, the device comprising:
    a pushing rod, the pushing rod having an opening therealong;
    a shaft disposed within at least a portion of the opening of the pushing rod;
    a shaft retaining element fixedly attached to the shaft;
    a pusher, the pusher fixedly attached to the pushing rod;
    a spring;
    a spring retainer, the spring biased against at least one surface of the spring retainer; and
    at least one retention element rotatably movable between a first and a second position, the at least one retention element engages the spring retainer and the shaft retaining element in the first position; and
    a seal assembly having a first portion and a second portion, the seal assembly operatively attached at the first portion to the distal end of the shaft, the seal assembly configured to engage the interior wall surface and the exterior wall surface of the blood vessel,
    wherein the pushing rod operatively engages the seal assembly at the second portion and is movable relative to the shaft, the at least one retention element rotating from the first position to the second position in response to the shaft moving distally.

7. The device for sealing an opening according to claim 6, wherein the at least one retention element comprises two retention elements.

8. The device for sealing an opening according to claim 6, wherein the at least one retention element has two legs, a first leg engaging the spring retainer and a second leg engaging the shaft retaining element.

9. The device for sealing an opening according to claim 8, wherein the second leg is longer than the first leg.

10. The device for sealing an opening according to claim 8, wherein each of the first and second legs have a flat surface at one end thereof.

11. The device for sealing an opening according to claim 6, further comprising a safety latch, the safety latch movable between a first position and a second position, the safety latch engaging a slot in the pusher thereby preventing the pusher from moving the pushing rod.

12. The device for sealing an opening according to claim 6, Wherein the at least one retention element engages a surface of the spring retainer and also engages a surface of the shaft retaining element in the first position.

* * * * *